(12) United States Patent
Bradley

(10) Patent No.: US 8,114,162 B1
(45) Date of Patent: Feb. 14, 2012

(54) SPINAL FUSION IMPLANT AND RELATED METHODS

(75) Inventor: W. Dan Bradley, Denton, TX (US)

(73) Assignee: NuVasive, Inc., San Diego, CA (US)

( * ) Notice: Subject to any disclaimer, the term of this patent is extended or adjusted under 35 U.S.C. 154(b) by 893 days.

(21) Appl. No.: 11/891,581

(22) Filed: Aug. 9, 2007

Related U.S. Application Data

(60) Provisional application No. 60/836,803, filed on Aug. 9, 2006.

(51) Int. Cl.
*A61F 2/44* (2006.01)

(52) U.S. Cl. .................. 623/17.16; 623/17.11

(58) Field of Classification Search ..... 623/17.11–17.16
See application file for complete search history.

(56) References Cited

U.S. PATENT DOCUMENTS

| | | |
|---|---|---|
| 4,493,317 A | 1/1985 | Klaue |
| 4,599,999 A | 7/1986 | Klaue |
| 4,743,256 A | 5/1988 | Brantigan |
| 4,904,261 A | 2/1990 | Dove et al. |
| 4,955,908 A | 9/1990 | Frey et al. |
| 5,364,399 A | 11/1994 | Lowery et al. |
| 5,397,364 A | 3/1995 | Kozak et al. |
| 5,405,391 A | 4/1995 | Hednerson et al. |
| 5,423,826 A | 6/1995 | Coates et al. |
| 5,507,801 A | 4/1996 | Gisin et al. |
| 5,578,034 A | 11/1996 | Estes |
| 5,601,553 A | 2/1997 | Trebing et al. |
| 5,616,144 A | 4/1997 | Yapp et al. |
| 5,713,899 A | 2/1998 | Marnay et al. |
| 5,755,721 A | 5/1998 | Hearn |
| 5,772,661 A | 6/1998 | Michelson |
| 5,851,207 A | 12/1998 | Cesarone |
| 5,876,402 A | 3/1999 | Errico et al. |
| 5,888,223 A | 3/1999 | Bray |
| 5,916,267 A | 6/1999 | Tienboon |
| 5,931,838 A | 8/1999 | Vito |
| 5,951,558 A | 9/1999 | Fiz |
| 5,954,722 A | 9/1999 | Bono |
| 6,066,175 A | 5/2000 | Henderson et al. |
| 6,080,193 A | 6/2000 | Hochshuler et al. |
| 6,093,205 A | 7/2000 | McLeod et al. |
| 6,120,503 A | 9/2000 | Michelson |
| 6,136,001 A | 10/2000 | Michelson |
| 6,139,550 A | 10/2000 | Michelson |
| 6,152,927 A | 11/2000 | Farris et al. |
| 6,156,037 A | 12/2000 | LeHuec et al. |
| 6,193,721 B1 | 2/2001 | Michelson |
| 6,210,415 B1 | 4/2001 | Bester |
| 6,228,118 B1 | 5/2001 | Gordon |
| 6,235,034 B1 | 5/2001 | Bray |
| 6,235,059 B1 | 5/2001 | Benezech et al. |
| 6,261,291 B1 | 7/2001 | Talaber et al. |

(Continued)

FOREIGN PATENT DOCUMENTS

EP 0179695 B1 3/1989

(Continued)

*Primary Examiner* — Eduardo C Robert
*Assistant Examiner* — Ellen C Hammond
(74) *Attorney, Agent, or Firm* — NuVasive, Inc.; Jonathan Spangler; Jennifer Russell

(57) ABSTRACT

A spinal fusion implant to be inserted within an intervertebral disc space in order to sustain spinal geometry and promote fusion of the adjacent vertebral bodies.

8 Claims, 5 Drawing Sheets

U.S. PATENT DOCUMENTS

| | | | |
|---|---|---|---|
| 6,306,139 B1 | 10/2001 | Fuentes | |
| 6,306,170 B2 | 10/2001 | Ray | |
| 6,331,179 B1 | 12/2001 | Freid et al. | |
| 6,342,055 B1 | 1/2002 | Eisermann et al. | |
| 6,342,057 B1 | 1/2002 | Brace et al. | |
| 6,364,880 B1 | 4/2002 | Michelson | |
| 6,379,364 B1 | 4/2002 | Brace et al. | |
| 6,398,783 B1 | 6/2002 | Michelson | |
| 6,413,259 B1 | 7/2002 | Lyons et al. | |
| 6,432,106 B1 | 8/2002 | Fraser | |
| 6,454,771 B1 | 9/2002 | Michelson | |
| 6,461,359 B1 | 10/2002 | Tribus et al. | |
| 6,471,724 B2 | 10/2002 | Zdeblick et al. | |
| 6,485,517 B1 | 11/2002 | Michelson | |
| 6,527,776 B1 | 3/2003 | Michelson | |
| 6,558,423 B1 | 5/2003 | Michelson | |
| 6,562,073 B2 | 5/2003 | Foley | |
| 6,572,619 B2 | 6/2003 | Santilli | |
| 6,576,017 B2 | 6/2003 | Foley et al. | |
| 6,579,290 B1 | 6/2003 | Hardcastle et al. | |
| 6,582,468 B1 | 6/2003 | Gauchet | |
| 6,602,255 B1 | 8/2003 | Campbell et al. | |
| 6,629,998 B1 | 10/2003 | Lin | |
| 6,669,700 B1 | 12/2003 | Farris et al. | |
| 6,682,563 B2 * | 1/2004 | Scharf | 623/17.16 |
| 6,692,503 B2 | 2/2004 | Foley et al. | |
| 6,695,846 B2 | 2/2004 | Richelsoph et al. | |
| 6,712,818 B1 | 3/2004 | Michelson | |
| 6,730,127 B2 | 5/2004 | Michelson | |
| 6,773,460 B2 | 8/2004 | Jackson | |
| 6,837,905 B1 | 1/2005 | Lieberman | |
| 6,896,676 B2 | 5/2005 | Zubok et al. | |
| 6,916,320 B2 | 7/2005 | Michelson | |
| 6,936,050 B2 | 8/2005 | Michelson | |
| 6,936,051 B2 | 8/2005 | Michelson | |
| 6,972,019 B2 | 12/2005 | Michelson | |
| 6,972,037 B2 * | 12/2005 | Zubok et al. | 623/17.15 |
| 6,972,038 B2 * | 12/2005 | Zubok et al. | 623/17.15 |
| 6,994,728 B2 * | 2/2006 | Zubok et al. | 623/17.15 |
| 6,994,729 B2 * | 2/2006 | Zubok et al. | 623/17.15 |
| 6,997,954 B2 * | 2/2006 | Zubok et al. | 623/17.15 |
| 6,997,955 B2 * | 2/2006 | Zubok et al. | 623/17.15 |
| 7,001,387 B2 | 2/2006 | Farris et al. | |
| 7,001,389 B1 | 2/2006 | Navarro et al. | |
| 7,004,944 B2 | 2/2006 | Gause | |
| 7,033,394 B2 | 4/2006 | Michelson | |
| 7,041,135 B2 | 5/2006 | Michelson | |
| 7,048,739 B2 | 5/2006 | Konieczynski et al. | |
| 7,060,067 B2 | 6/2006 | Needham et al. | |
| 7,112,222 B2 | 9/2006 | Fraser et al. | |
| 7,137,984 B2 | 11/2006 | Michelson | |
| 7,163,561 B2 | 1/2007 | Michelson | |
| 7,172,627 B2 | 2/2007 | Fiere et al. | |
| 7,175,662 B2 * | 2/2007 | Link et al. | 623/17.11 |
| 7,182,782 B2 | 2/2007 | Kirschman | |
| 7,198,643 B2 * | 4/2007 | Zubok et al. | 623/17.15 |
| 7,204,837 B2 | 4/2007 | Paul | |
| 7,226,452 B2 * | 6/2007 | Zubok et al. | 606/99 |
| 7,232,464 B2 | 6/2007 | Mathieu et al. | |
| 7,238,203 B2 | 7/2007 | Bagga et al. | |
| 7,255,698 B2 | 8/2007 | Michelson | |
| 7,320,708 B1 | 1/2008 | Bernstein | |
| 7,331,994 B2 | 2/2008 | Gordon et al. | |
| 7,354,452 B2 | 4/2008 | Foley | |
| 7,452,370 B2 | 11/2008 | Anderson | |
| 7,566,346 B2 * | 7/2009 | Kirschman | 623/17.14 |
| 7,594,931 B2 * | 9/2009 | Louis et al. | 623/17.11 |
| 7,618,456 B2 | 11/2009 | Mathieu et al. | |
| 7,662,174 B2 | 2/2010 | Doubler et al. | |
| 2002/0128715 A1 * | 9/2002 | Bryan et al. | 623/17.15 |
| 2002/0143399 A1 * | 10/2002 | Sutcliffe | 623/17.11 |
| 2003/0083667 A1 | 5/2003 | Ralph | |
| 2003/0167091 A1 * | 9/2003 | Scharf | 623/17.11 |
| 2003/0187440 A1 | 10/2003 | Richelsoph | |
| 2003/0225409 A1 | 12/2003 | Freid | |
| 2004/0039387 A1 | 2/2004 | Gause | |
| 2004/0186482 A1 | 9/2004 | Kolb | |
| 2004/0193272 A1 | 9/2004 | Zubok | |
| 2004/0210232 A1 | 10/2004 | Patel | |
| 2004/0215195 A1 | 10/2004 | Shipp | |
| 2004/0267274 A1 | 12/2004 | Patel | |
| 2005/0015092 A1 | 1/2005 | Rathbun | |
| 2005/0015093 A1 | 1/2005 | Suh | |
| 2005/0027301 A1 | 2/2005 | Stihl | |
| 2005/0033294 A1 | 2/2005 | Garden | |
| 2005/0038444 A1 | 2/2005 | Binder | |
| 2005/0043738 A1 | 2/2005 | Ryan | |
| 2005/0049593 A1 | 3/2005 | Duong | |
| 2005/0137606 A1 | 6/2005 | Binder | |
| 2005/0143824 A1 | 6/2005 | Richelsoph | |
| 2005/0234455 A1 | 10/2005 | Binder et al. | |
| 2005/0261690 A1 | 11/2005 | Binder et al. | |
| 2006/0030851 A1 | 2/2006 | Bray | |
| 2006/0079961 A1 | 4/2006 | Michelson | |
| 2006/0100637 A1 | 5/2006 | Rathbun | |
| 2006/0129244 A1 | 6/2006 | Ensign | |
| 2006/0206208 A1 | 9/2006 | Michelson | |
| 2006/0224241 A1 | 10/2006 | Butler | |
| 2006/0235403 A1 | 10/2006 | Blain | |
| 2006/0235409 A1 | 10/2006 | Blain | |
| 2007/0055252 A1 | 3/2007 | Blain | |
| 2007/0233120 A1 | 10/2007 | Thramann | |
| 2008/0097433 A1 | 4/2008 | Molz | |
| 2008/0119933 A1 | 5/2008 | Aebi et al. | |
| 2008/0161925 A1 | 7/2008 | Brittan | |
| 2008/0177307 A1 | 7/2008 | Moskowitz | |
| 2008/0249569 A1 | 10/2008 | Waugh et al. | |
| 2008/0249575 A1 | 10/2008 | Waugh et al. | |
| 2008/0249625 A1 | 10/2008 | Waugh et al. | |
| 2008/0287999 A1 | 11/2008 | Markworth | |
| 2008/0306596 A1 | 12/2008 | Jones | |
| 2009/0088849 A1 | 4/2009 | Armstrong et al. | |
| 2009/0210064 A1 | 8/2009 | Lechmann et al. | |
| 2009/0264934 A1 | 10/2009 | Youssef et al. | |
| 2010/0042159 A1 | 2/2010 | Butler | |
| 2010/0057206 A1 | 3/2010 | Duffield et al. | |
| 2010/0087925 A1 | 4/2010 | Kostuik et al. | |
| 2010/0094421 A1 | 4/2010 | Mathieu et al. | |
| 2010/0121383 A1 | 5/2010 | Stanaford et al. | |

FOREIGN PATENT DOCUMENTS

| | | |
|---|---|---|
| WO | 2007098288 A2 | 8/2007 |
| WO | 2008065450 | 6/2008 |
| WO | 2009064644 A1 | 5/2009 |
| WO | 2009148421 A1 | 12/2009 |
| WO | 2010028095 A1 | 3/2010 |
| WO | 2010054181 A1 | 5/2010 |
| WO | 2010054208 A1 | 5/2010 |

* cited by examiner

SPINAL FUSION IMPLANT AND RELATED METHODS

CROSS REFERENCES TO RELATED APPLICATIONS

The present application is a non-provisional patent application claiming benefit under 35 U.S.C. §119(e) from U.S. Provisional Application Ser. No. 60/836,803, filed on Aug. 9, 2006, the entire contents of which are hereby expressly incorporated by reference into this disclosure as if set forth fully herein.

BACKGROUND OF THE INVENTION

I. Field of the Invention

The present invention relates generally to spinal surgery and, more particularly, to a device for spinal fusion comprising a spinal fusion implant to be inserted into the cervical, thoracic or lumbar disc spaces.

II. Discussion of the Prior Art

Approximately 500,000 lumbar and cervical fusion procedures are performed each year in the United States to correct problems with displaced, damaged, or degenerated intervertebral discs due to trauma, disease, or aging. Commonly, spinal fusion procedures involve removing some or the all of a diseased or damaged vertebral disc followed by insertion of an implant into the evacuated disc space.

Anterior lumbar intervertebral-body fusion (ALIF) procedures present one manner of gaining surgical access to an affected vertebral joint. The ALIF technique involves approaching the spine through the abdomen, as opposed to approaching from the patient's side or back. Most commonly ALIF procedures result in the implantation of a disc space insert. Once introduced, the implant serves to restore disc space height and promote fusion across the affected joint, creating a long term solution designed to reduce if not eliminate neural impingement arising from an affected disc.

Multiple implant designs are currently used in conjunction with the ALIF procedure. Of the implant designs in existence, the most commonly used ALIF disc space implant design comprises a disc space insert dimensioned to fit entirely within and maintain disc space height and promote fusion across the affected vertebral joint.

While insertion of a single disc space implant residing entirely within the disc space is widely accepted and utilized, occasionally the demands of a given affected joint require supplemental implant support. It is not uncommon, for example, for a plate (spanning over the disc space and coupled to the adjacent vertebral bodies) to be used to augment the support provided by the interbody implant. Although introduction of multiple implants has been successfully used to treat spinal malformations, other spinal procedures benefit from the use of a permanently configured, single appliance to achieve the functionality provided by an implant/plate combination.

Various efforts have been undertaken in the prior art at providing combination implants comprised of an interbody region coupled with a "plate" region configured to affix the implant to adjacent vertebral bodies. While the present combination implants are generally effective, there nonetheless exists a need for improved combination implants.

SUMMARY OF THE INVENTION

The present invention addresses this need by providing a spinal fusion implant for placement between adjacent vertebral bodies having an interbody region and two flange regions extending from diametrically opposed aspects of a trailing edge of the interbody region. In other words, the two flange regions are offset from the midline of the trailing edge of the interbody region, with one flange region extending upwards from an upper surface of the trailing edge and one flange region extending downwards from a lower surface of the trailing edge. The interbody region also preferably includes two screw apertures located slightly offset (horizontally, that is) with apertures formed in the two flange regions. The two screw apertures extend in an angled manner through the trailing edge of the interbody region, such that a screw introduced through the first aperture passes angularly downwards towards the lower flange region and into the lower vertebral body and a screw introduced through the second aperture passes angularly upwards towards the upper flange region and into the upper vertebral body.

The implant of the present invention may also include apertures through which a clinician might introduce fusion inducing materials or other post insertion therapeutic materials. The spinal fusion implant of the present invention may be comprised of any suitable non-bone composition, including but not limited to polymer compositions (e.g. poly-ether-ether-ketone (PEEK) and/or poly-ether-ketone-ketone (PEKK)), ceramic, metal, or any combination of these materials. The spinal fusion implant of the present invention may be provided in any number of suitable shapes and sizes depending upon the particular surgical procedure or need. The spinal fusion implant may be dimensioned for use in various regions of the spine without departing from the scope of the present invention. Furthermore, the implant may comprise any number of additional utility apertures through which additional therapeutic materials and or work might be accomplished.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be that such a development effort might be complex and time-consuming, but would nevertheless be a routine undertaking for those of ordinary skill in the art having the benefit of this disclosure. The spinal fusion implant disclosed herein boasts a variety of inventive features and components that warrant patent protection, both individually and in combination.

Figure 1:
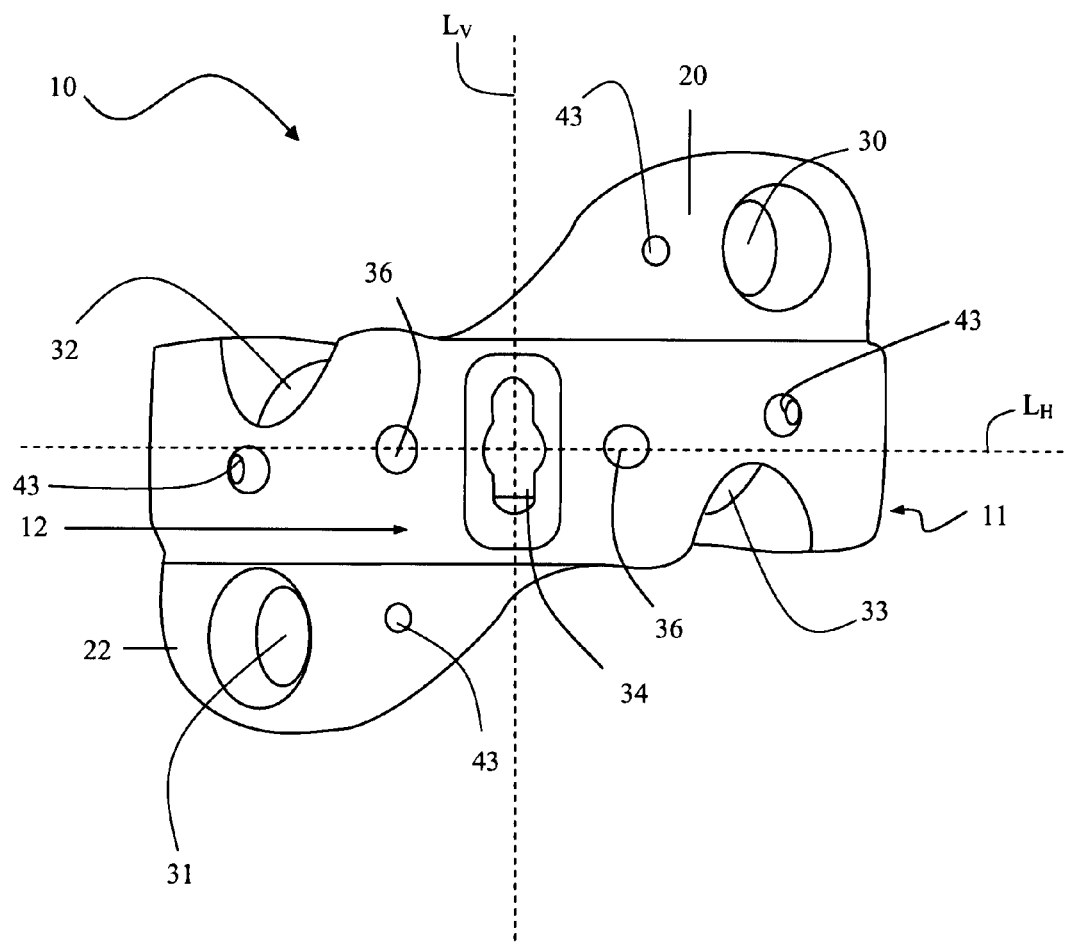
FIG. 1 is a front view of the spinal fusion implant according to one embodiment of present invention.
Figure 2:
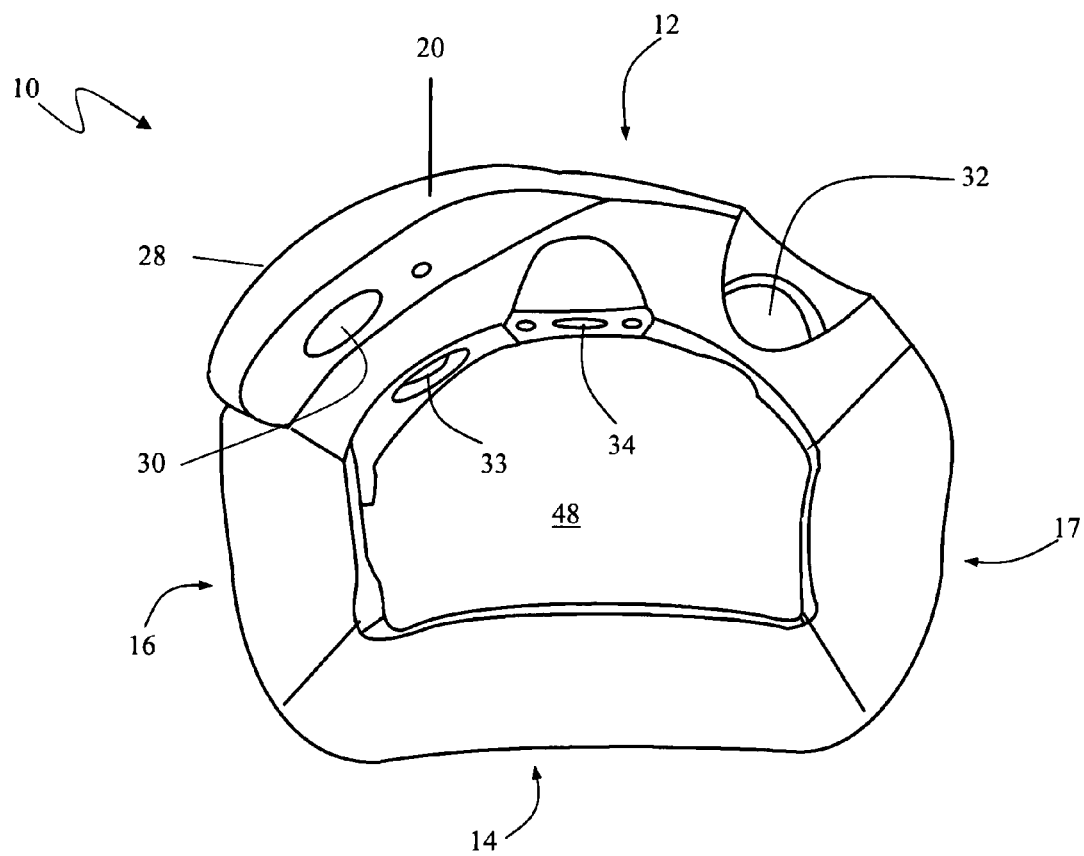
FIG. 2 is a top view of the spinal fusion implant of FIG. 1.
Figure 3:
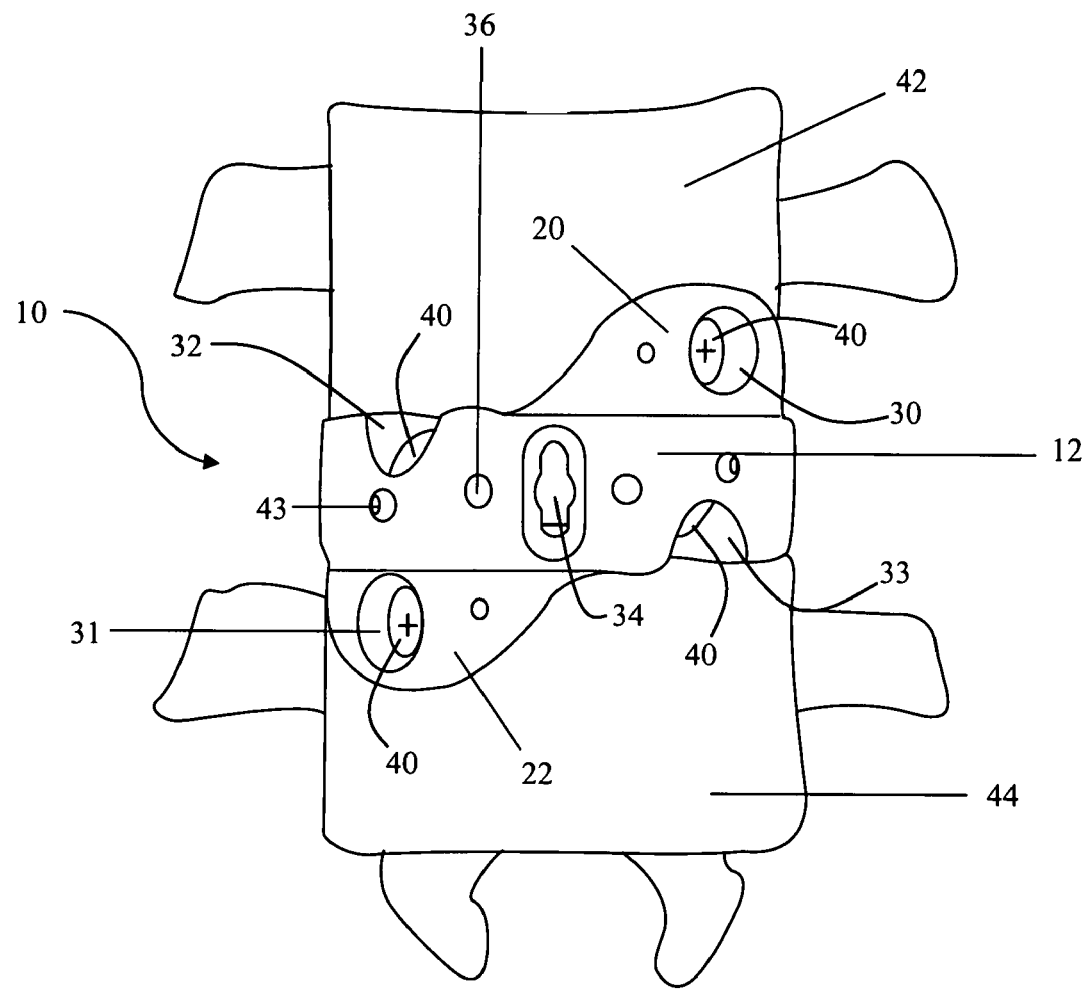
FIG. 3 is a front view of the spinal fusion implant of FIG. 1 implanted in a human spine.

FIGS. 1-3 illustrate one example of a spinal fusion implant 10 according to a first broad aspect of the present invention. The spinal fusion implant 10 of the present invention includes an interbody region 11 having a trailing end 12, a superior flange member 20 extending from a superior aspect of the trailing end 12, and an inferior flange member 22 extending from an inferior aspect of the trailing end 12. For the purposes of illustration, the spinal fusion implant may be divided into superior and inferior aspects by a horizontal midline $L_H$ and into first and second lateral aspects by a vertical midline $L_V$. The superior flange 20 is generally provided in a first lateral aspect of the implant 10 and includes a first fixation aperture 30 dimensioned to receive a fixation element 40. The inferior flange 22 is generally provided in a second lateral aspect of the implant 10 such that the superior flange 20 and the inferior flange 22 are diametrically opposed from one another across the vertical midline $L_V$. The inferior flange 22 includes a second fixation aperture 31 dimensioned to receive a fixation element 40. As shown, the fixation apertures 30, 31 are configured to direct screw insertion generally perpendicularly into the adjacent vertebrae 42, 44 with fixation elements 40 inserted therein.

The trailing end 12 is further equipped with first and second supplemental fixation apertures 32, 33, each dimensioned to receive a fixation element in order to fix the implant preferentially in place. The first supplemental fixation aperture 32 is offset superiorly from the horizontal midline $L_H$ and positioned in the second lateral aspect (opposite the vertical midline $L_V$ from the superior flange 20). The second supplemental fixation aperture 33 is offset inferiorly from the horizontal midline $L_H$ and positioned in the first lateral aspect (opposite the vertical midline $L_V$ from the inferior flange 22). First and second supplemental fixation apertures 32, 33 are oriented in an angled relationship to the exterior surface 28 of the implant 10 and extend from the exterior surface 28 into the fusion chamber 48 (described in further detail below). As illustrated in FIGS. 1-3, in one embodiment the supplemental fixation apertures 32, 33 may be angled such that a fixation element 40 applied thereto would pass at least partially through the disc space and into the vertebral body located opposite the horizontal midline $L_H$ from the respective supplemental fixation aperture 32, 33. For example, the first supplemental fixation aperture 32 (positioned superiorly of horizontal midline $L_H$) is angled such that a fixation element 40 inserted therethrough would pass at least partially through the intervertebral disc space and into inferior vertebra 44. Likewise, the second supplemental fixation aperture 33 (positioned inferiorly of horizontal midline $L_H$) is angled such that a fixation element 40 inserted therethrough would pass at least partially through the intervertebral disc space and into superior vertebra 42.

Although the implant 10 is shown as having the general fixation aperture configuration described above, it can be appreciated that any number of additional fixation apertures may be included in any angular orientation within the trailing end 12. Whereas the example shown in FIGS. 1-3 illustrates the inclusion of fixation apertures solely within the trailing end 12, alternative embodiments of the present invention may comprise any number of fixation apertures provided within any surface of the implant 10 as preferred or necessary in light of the structure of the adjacent receiving tissue.

The implant 10 may further include an insertion aperture 34 dimensioned to receive at least a portion of an insertion tool for inserting the implant 10 into a target disc space. By way of example only, the insertion aperture 34 is shown in FIG. 1 as positioned in the trailing end 12 at the intersection of the horizontal midline $L_H$ and the vertical midline $L_V$. However, positioning of the insertion aperture 34 may occur at any suitable place along the interbody region 11. Upon removal of the insertion tool after implantation of the spinal fusion implant 10, the insertion aperture 34 may act as a utility aperture or a viewing aperture. Although presently illustrated as fully extending through the implant 10, it can be appreciated the insertion aperture 34 may only partially extend into the implant 10. Moreover although illustrated as including a single insertion aperture 34, it can be appreciated that the implant 10 may include additional insertion apertures located on any exterior surface suitably positioned to allow for advantageous manipulation of the implant 10 during implantation. Additionally, the spinal fusion implant 10 may be provided with at least one viewing aperture 36 dimensioned and positioned to allow a physician to inspect for post-implantation fusion.

A plurality of utility apertures 43 located in at least one of the interbody region 11, the superior flange 20, and the inferior flange 22 may be provided. The utility apertures 43 may serve a variety of functions including but not limited to (and by way of example only) providing an access point to tissue bounded by the implant for the insertion of instruments, therapeutic materials (such as bone growth promoting material or antibiotics) and implants. Therefore it can be appreciated that the utility apertures 43 may comprise any suitable shape including but not limited to rectangular, triangular and the like extending in any number of angles as required by the clinician to effect preferential treatment of the affected spinal area.

The interbody region 11 further includes a first side 16, a second side 17, and a leading end 14 that, along with the trailing end 12, collectively define the boundaries of a fusion chamber 48 comprising an interior aspect of the implant 10. As shown in FIG. 3, upon implantation the spinal fusion implant 10 at least partially engages the superior surface of the adjacent inferior vertebra 44 and the inferior surface of the adjacent superior vertebra 42, an engagement which in effect defines the superior and inferior boundaries of fusion chamber 48, while providing interaction between fusion chamber 48 and the vertebrae 42, 44. Once established, the fusion chamber 48 may act as a conduit through which fusion might take place. In the alternative, the fusion chamber 48 may be provided with fusion inducing materials including but not limited to bone morphogenic protein (BMP), cancellous or autograft bone, hydroxyapatite, coral or any other natural or synthetic osteoinductive material inserted therein to promote fusion across the affected intervertebral disc space.

The present embodiment of the spinal fusion implant 10 illustrates, by way of example only, the inclusion of a single superior flange 20 extending from the trailing end 12 superiorly and in contact with the surface of the adjacent superior vertebral body 42. The superior flange 20 as illustrated comprises a single fixation aperture 30 and a single utility aperture 43. Configured in this manner, the superior flange 20 provides an implant extension through which fixation elements 40 can be inserted to affix the implant to the superior vertebral body 42. Although presented in the current embodiment as comprising a single fixation aperture 30 and single utility aperture 43, it can be appreciated that any number and combination of fixation apertures 30 and utility apertures 43 might be included within the superior flange 20.

Likewise, the present embodiment of the spinal fusion implant 10 illustrates, by way of example only, the inclusion of an inferior flange member 22 extending inferiorly from the trailing end 12 and in contact with the surface of the adjacent inferior vertebral body 44. Configured in this manner, the inferior flange member 22 provides an implant extension through which fixation elements 40 can be inserted to affix the implant to the inferior vertebral body 44. Although presented in the current embodiment as comprising a single fixation aperture 31 and single utility aperture 43, it can be appreciated that any number and combination of fixation apertures 31 and utility 43 apertures might be included within the inferior flange member 22.

Although constructed in the aforementioned configuration it can be appreciated that the implant 10 may comprise any number of flange members 20, 22 attached at any number of positions on the implant 10 as needed. Furthermore, the flange members 20, 22 may comprise any shape and size suitable to facilitate preferential fixation of the implant 10 to the vertebral bodies. For example, the superior 20 and inferior 22 flange members may be shaped to conform to the natural curvature of the vertebral body surfaces 42, 44 with which they are aligned.

As illustrated in the current embodiment, the fixation apertures 30, 31, 32, 33 of the present invention comprise generally cylindrical spaces extending from the outer implant surface 28 to the inner implant surface 26 to receive a fixation element 40 such as a bone screw. Although illustrated as a smooth bored generally cylindrical structure, the fixation apertures 30, 31, 32, 33 may comprise any structure including but not limited to threads, ratcheting elements and the like or be treated with any substance for example only as bio compatible adhesives which might support a fixation device therein. Moreover the fixation apertures 30, 31, 32, 33 may comprise any dimension which suitably accepts the chosen fixation element 40.

Although presented as bone screws in the current embodiment, suitable fixation elements 40 may include but are not limited to screws, pins, nails, wire, staples, sutures adhesives or any similar device capable of preferentially securing the spinal fusion implant 10 to the vertebrae 42, 44. Additionally, the fixation elements 40 may be composed of titanium, steel, aluminum, bone, bioresorbable matter or any other material suitable for optimally fixing the implant in a preferred position. Furthermore, some or all of the fixation elements 40 may be removable or permanent and/or variable or fixed angle fixation elements.

Figure 4:
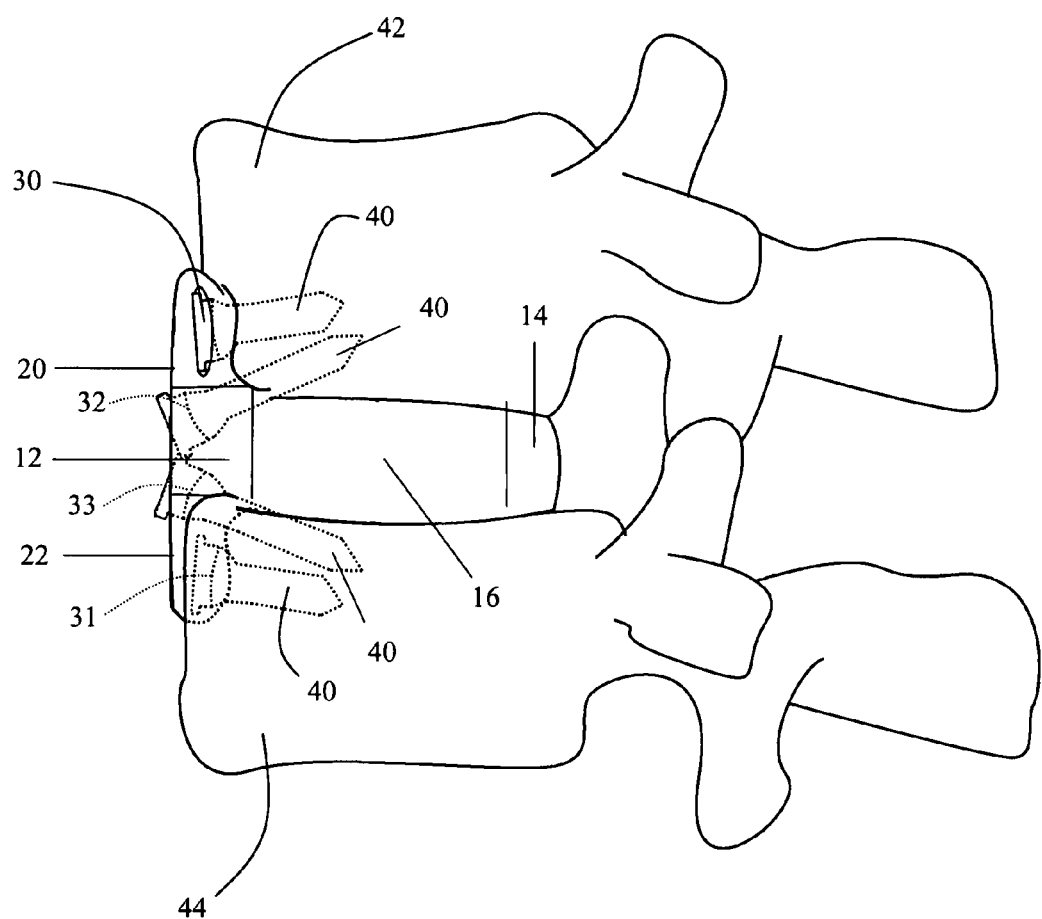
FIG. 4 is a side view of the spinal fusion implant of FIG. 1 implanted in a human spine.

FIG. 4 illustrates one example of a further embodiment of the current invention inserted within an affected disc space. As illustrated, the implant 10 comprises a leading end 14, a first side 16, a second side 17 (not shown), and a trailing end 12 comprising first and second supplemental fixation apertures 32, 33. The current implant 10 also comprises a superior and an inferior flange member 20, 22 comprising a fixation apertures 30, 31, respectively. In this example, the fixation aperture 30 directs fixation element 40 into the superior vertebral body 42 at an angle generally not perpendicular to the outer surface of the implant 10. Additionally, the first supplemental aperture 32 is oriented to direct fixation element 40 into the superior vertebral body 42. As shown, the fixation aperture 31 directs fixation element 40 into the inferior vertebral body 44 at an angle generally not perpendicular to the outer surface of the implant 10. Presently configured, the second supplemental fixation aperture 33 is oriented to direct fixation element 40 into the inferior vertebral body 44.

Figure 5:
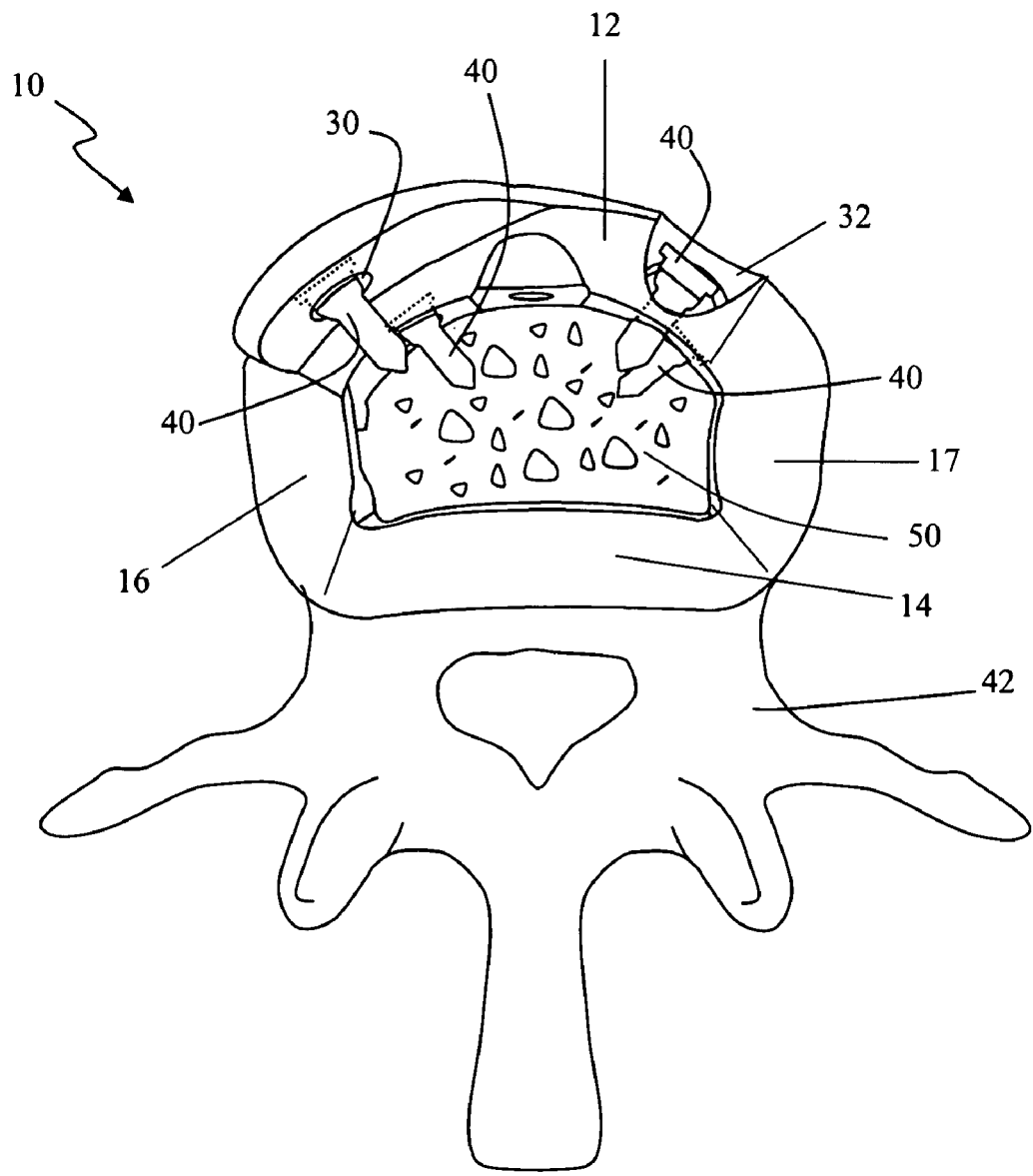
FIG. 5 is a top view of the spinal fusion implant of FIG. 1 implanted in a human spine.

FIG. 5 illustrates one example of an alternative embodiment of the invention inserted within an affected disc space, with the superior vertebra 42 removed for viewing. As configured, the implant 10 comprises a trailing end 12, leading end 14, and sides 16, 17 defining the boundaries of the fusion chamber 48. As shown, the fusion chamber 48 includes fusion inducing materials 50. Although the current embodiment describes a fully bounded fusion chamber 48, it can be appreciated that the implant 10 may only partially bound the radial extent of the fusion chamber 48.

According to a broad aspect of the present invention, the spinal fusion implant 10 is introduced into a spinal target site after creation of a suitably dimensioned surgical corridor and preparation of the implant receiving disc space. A single spinal fusion implant 10 is then passed through the surgical corridor and placed into the prepared intervertebral disc space utilizing an implantation device configured for use in conjunction with the insertion aperture 34. Although implantation is described using an insertion tool interacting with the insertion aperture 34, it can be appreciated that alternative implantation devices and/or mechanisms may be used to achieve implantation without utilizing the insertion aperture 34.

Once the spinal fusion implant 10 has been preferentially positioned within the target intervertebral space, the fixation elements 40 are inserted into the first and second fixation apertures 30, 31 and/or first and second supplemental fixation apertures 32, 33, and then driven into the respective vertebrae using an insertion apparatus such as by way of example only, a screw driver. By way of example only, implantation of the implant 10 of FIGS. 1-2 may be achieved through insertion of a first screw 40 through the first fixation aperture 30, then a second screw 40 through the second fixation aperture 31, followed by a third screw 40 through the first supplemental fixation aperture 32 then a fourth screw 40 through the second supplemental fixation aperture 33. Although shown in the above mentioned sequence it can be appreciated that any number of sequences may be used to accomplish preferential implant 10 fixation. Moreover, the various fixation apertures may include structures such as threads, treatments or appliances which would allow for at least partial pre-implantation insertion of fixation elements 40 within the fixation apertures 30, 31, 32, 33. Configured thusly, the implant, with fixation elements 40 partially inserted within the various fixation apertures would be inserted within the affected disc space, preferentially aligned with the vertebrae 42, 44, followed by driving the insertion elements 40 into the bone.

After insertion of the implant 10, therapeutic materials such as fusion inducing materials or drugs, may be introduced into the fusion chamber 48 through the insertion device aperture 34 and/or the viewing aperture 36. Insertion may be achieved by detachably providing an amount of therapeutic material of suitable dimension to pass through the targeted aperture 34, 36 to an appropriate insertion device also dimensioned to pass through the targeted aperture, and then passing the fusion inducing material and/or at least a portion of the insertion device through the aperture 34, 36, ultimately releasing the therapeutic material within the fusion chamber 48.

Alternatively, introduction of therapeutic material into the fusion chamber 48 may be achieved without introduction of an insertion device into said chamber 48. The current alternative method achieves insertion through aligning a pressure applying appliance containing the therapeutic materials with the intended aperture 34, 36 in communication with the fusion chamber 48. Subsequently, application of pressure to said material forces said material through the aperture 34, 36 and into the fusion chamber 48. Any suitable insertion device capable of directing the therapeutic material through the aperture 34, 36 under pressure may be employed, including but not limited to syringes, bulbs, tubes and the like.

The spinal fusion implant 10 may be provided with varying length and width dimensions depending upon the desired restored dimensions of the target disc space. Additionally the spinal fusion implant 10 of the illustrated and alternative embodiments may comprise any suitable bone or non-bone composition having suitable radiolucent characteristics, including but not limited to polymer compositions (e.g. poly-ether-ether-ketone (PEEK) and/or poly-ether-ketone-ketone (PEKK)) or any combination of PEEK and PEKK, plastics, ceramics, or metals.

The spinal fusion implant 10 may be provided with varying length and width dimensions depending upon the desired restored dimensions of the target disc space. Although shown and described herein within the context of an anterior approach (ALIF), it is to be understood and appreciated that the implant 10 of the present invention may be dimensioned for use in any additional types of surgical approaches, including lateral approach and antero-lateral approach. Additionally the spinal fusion implant 10 of the illustrated and alternative embodiments may comprise any suitable bone or non-bone composition having suitable radiolucent characteristics, including but not limited to polymer compositions (e.g. poly-ether-ether-ketone (PEEK) and/or poly-ether-ketone-ketone (PEKK)) or any combination of PEEK and PEKK, plastics, ceramics, or metals.

What is claimed is:

1. An implant dimensioned for insertion at least partially between adjacent first and second vertebral bodies comprising:
   an implant region dimensioned to be inserted at least partially within the disc space, comprising first and second lateral sides, a leading end, a trailing end, and opposing superior and inferior surfaces at least partially engaging the surfaces of the adjacent vertebral bodies from within the disc space, the trailing end comprising a superior supplemental fixation aperture and an inferior supplemental fixation aperture, each dimensioned to receive a fixation element;
   a first flange region extending superiorly from the trailing end of the implant and dimensioned to engage at least a portion of the first vertebral body, the first flange region including a first fixation aperture dimensioned to receive a fixation element; and
   a second flange region diametrically opposed from the first flange region and extending inferiorly from the trailing end of the implant and dimensioned to engage at least a portion of the second vertebral body, the second flange region including a second fixation aperture dimensioned to receive a fixation element;
   wherein the superior supplemental fixation aperture is positioned at a predetermined angle to effect insertion of a fixation element at least partially through the intervertebral disc space into the second vertebral body and the inferior supplemental fixation aperture is positioned at a predetermined angle to effect insertion of a fixation element at least partially through the intervertebral disc space into the first vertebral body.

2. The implant of claim 1, wherein the fixation aperture of the first flange is positioned in a first predetermined angle to effect insertion of a fixation element into the adjacent superior vertebral body, and the fixation aperture of the second flange is positioned in a second predetermined angle to effect insertion of a fixation element into the adjacent inferior vertebral body.

3. The implant of claim 2, wherein the first and second predetermined angles are at least one of equivalent and non-equivalent.

4. The implant of claim 1, wherein at least one of the first fixation aperture, the second fixation aperture, and the supplemental fixation aperture comprises any one of a threaded, ratcheting and anti back-out structure.

5. The implant of claim 1, wherein the implant comprises a fusion chamber radially defined by the leading end, trailing end, and first and second sides, the fusion chamber dimensioned to be at least partially in communication with the surfaces of the first and second vertebral bodies.

6. The implant of claim 1, wherein the implant further comprises an insertion aperture extending through the trailing end and dimensioned to receive at least a portion of an insertion tool.

7. The implant of claim 1, wherein the fixation elements comprise any one of a screw, nail, wire, stable, suture tack and rivet.

8. The implant of claim 1, wherein the implant comprises at least one of an allograft bone, autograft bone, polymer composition, plastic, ceramic, carbon fiber and metal.

* * * * *